United States Patent [19]
Conia et al.

[11] Patent Number: 5,972,667
[45] Date of Patent: Oct. 26, 1999

[54] METHOD AND APPARATUS FOR ACTIVATING A THERMO-ENZYME REACTION WITH ELECTROMAGNETIC ENERGY

[75] Inventors: Jérôme Conia; Claude Larry Keenan, both of Albuquerque, N.Mex.

[73] Assignee: Cell Robotics, Inc., Albuquerque, N.Mex.

[21] Appl. No.: 09/082,124

[22] Filed: May 19, 1998

[51] Int. Cl.$^6$ .............................. C12N 13/00; C12Q 1/68
[52] U.S. Cl. ........................ 435/173.2; 435/6; 435/173.1
[58] Field of Search .............................. 435/173.2, 173.1, 435/283.1

[56] References Cited

U.S. PATENT DOCUMENTS

| | | | |
|---|---|---|---|
| 4,629,687 | 12/1986 | Schindler et al. | 435/4 |
| 4,893,886 | 1/1990 | Ashkin et al. | 350/1.1 |
| 5,170,890 | 12/1992 | Wilson et al. | 209/301 |
| 5,283,417 | 2/1994 | Misawa et al. | 219/121.85 |
| 5,587,128 | 12/1996 | Wilding et al. | 422/50 |

OTHER PUBLICATIONS

A. J. Welch et al; Laser Thermal Ablation; 1991; pp. 815–823.

Michael W. Berns et al, Laser Microsurgery in Cell and Development Biology; 1981; pp. 505–513.

Klaus Rink et al; 1.48 μm Diode Laser Microdissection of the Zona Pellucida of Mouse Zygotes; 1994; pp. 412–422.

Michael R. Emmert–Buck et al; Laser Capture Microdissection; Nov. 8, 1996; pp. 998–1001.

Brian Matsumoto et al; Theory and Applications of Confocal Microscopy; 1994; pp. 190–198.

*Primary Examiner*—Lisa B. Arthur
*Assistant Examiner*—Jehanne Souaya
*Attorney, Agent, or Firm*—Robert W. Becker & Associates

[57] ABSTRACT

A method and apparatus for activating a thermo-enzyme reaction, such as a polymerase chain reaction or other temperature-sensitive transformation of biological systems are provided. Electromagnetic energy is applied to a target to produce a rapid elevation in the temperature of at least a portion of the target. The electromagnetic energy can be laser energy provided via a laser beam supplied from one or more laser sources. The laser beam can have a wavelength in the infrared range from 750 nm to mm. The source of electromagnetic energy can be used in association with a microscope and/or objective lens to irradiate microscopic targets.

12 Claims, 4 Drawing Sheets

METHOD AND APPARATUS FOR ACTIVATING A THERMO-ENZYME REACTION WITH ELECTROMAGNETIC ENERGY

BACKGROUND OF THE INVENTION

The present invention relates to a method and apparatus for activating a thermo-enzyme reaction by applying electromagnetic energy to a target to produce a rapid elevation in the temperature of at least a portion of the target.

The present invention is applicable to certain temperature-sensitive transformations of biological systems. For example, the present invention is applicable to the temperature-sensitive transformation of cells with the specific synthesis or activation of bio-molecules such as enzymes and/or structural heat shock proteins. A number of thermally-induced reactions that in turn activate or regulate other enzyme activities in biological systems are of importance for the induction of various molecular syntheses or molecular processings. Some genetic mutations may be revealed following temperature changes of a few degrees centigrade which result in the production of new structural proteins that participate in the membranous assembly of a cell and therefore can be used for diagnostic purposes. Some heat shock proteins are specific to cancer or to infectious pathogens and constitute valuable markers capable of eliciting immune responses. Heat shock protein syntheses or processings can be made to occur in vitro in experimental systems, in living cells and tissues, or in intact organisms. Typically, specimens are exposed to non-lethal temperature variations from 1 to 20° C. circa the optimum temperature conditions for the observed specimens (i.e. 37° C. for specimen of human origin) for periods from several seconds to several hours duration. The ability to report the protein products using a variety of biochemical, histological, and/or microscopy techniques, allows for the identification of specific heat induced markers. These markers can be used for diagnostically detecting genetic mutations, such as, but not limited to, cancer and other inheritable diseases. Identified markers are also useful to assist in developing techniques for gene therapy, and to diagnose the presence of pathogens responsible for a variety of diseases including, but not limited to, HIV, malaria, hepatitis, and other bacteria-mediated diseases. Nonetheless, current methodologies for experimental thermal induction of biological reactions have limits. These reactions are typically induced by mass temperature increases or decreases that affect entire populations of cells, large tissue specimens, or even intact live animals. By contrast, the present invention teaches a new method for temperature control using the property of energy transfer from a radiative source of infrared light directed to at least a portion of a microscopic target or to single cells.

The present invention is particularly applicable to thermo-enzyme cycling reactions, especially the amplification of nucleic acids into polynucleotides using polymerase chain reaction (PCR).

Polymerase chain reaction (PCR) is a method for the in vitro synthesis of nucleic acids. A particular segment of DNA or RNA is specifically extended or replicated in vitro during a repeated and thermally controlled enzymatic reaction. Successive cycles of amplification, which refers to the accumulation of identical copies of a nucleic acid template by repetitive duplication of the template and its copies, and encompasses the three phases of denaturation, annealing, and extension, double the amount of the target DNA synthesized in the previous cycle. Procedures are well established and a significant product yield is possible even when starting with an extremely small amount of template.

Applications for PCR technologies are found in various domains of research and diagnostics, including sequencing or mutagenesis of genetic material, analysis and diagnosis of genetic disorders and diseases, forensics and evolutionary investigations. The societal benefits of PCR have been well documented with respect to quality testing and for various diagnoses, for example with the detection of microorganisms such as bacteria and viruses in water supplies and with the early detection of cancer or of diseases.

Optimization of PCR reactions requires decisive control over several parameters. The occurrence of artifacts is limited with properly defined concentration requirements for enzyme, molecular reagents including template sequence, salts, and for the buffer solution. Most importantly, precise control over the temperature of the reaction during its entire duration is critical to the successful production of highly specific products. Repeated cycles of heating and cooling are necessary for the complete denaturation of the template molecules, for the reliable annealing of the primers to their complementary sequences and for their correct extension with the action of the DNA polymerase. It is also important to select a reaction vessel with fast thermal transmission characteristics and minimum thermal capacity to avoid absorption from the heat source. Typical denaturation conditions vary from 94° C. to 99° C. and between from a few seconds to a minute. Typical annealing conditions vary between 55° C. and 75° C. and require from a few seconds to one minute to complete. Optimum annealing temperature must be determined precisely to assure best product yield. The correct extension of the primers also depends upon the temperature of the reaction and is usually performed between about 70° C. and 75° C.

DNA amplification can be performed directly in individual cells and tissue sections on a microscope slide. In situ PCR makes the detection of specific nucleic acid sequences highly sensitive and fast. Current methods involve the thermal cycling of the entire slide specimen that is placed in contact with a thermocycler's heater block. Evaporation control devices must be added to the slide, such as a layer of wax or a self-adhesive chamber device. Typically the entire specimen is exposed to the thermal cycling. In contrast, the present invention proposes to limit the thermal cycling phenomenon to the cell chromosome or target of interest by the irradiation profile of a controlled source of electromagnetic energy.

During the entire duration of the amplification process, different precise temperature levels must be rapidly reached and stabilized for well defined periods of time in a cyclical manner for the denaturation, annealing and extension phases. To achieve this, commercially available automated instruments known as thermocyclers are preferred to less accurate manual methods in which reaction vessels containing the reagents are systematically transferred between water baths that are maintained at different temperatures. The technical requirements for automated or semi-automated instruments include a regulated heater or heat source with associated monitoring device, a timer, a reaction chamber and possibly a programmable controller. The reaction vessels have fast thermal transmission characteristics and minimal thermal capacity. Using micro-capillary tubes to contain the reaction or thin walled microcentrifuge tubes with a high surface area to volume ratio cuts sample temperature lag. Temperature elevation is obtained via conduction or convection phenomena. In the conduction design, the reaction vessels are placed in direct contact with the heater element, a conventional design of which includes a single heat block with integrated cooling provided by circulation of refrigerant or of tap water. In the convection design, heat transfer to the reaction vessels is via a fluid such as oil, a polymer or simply a layer of air. The combination of high velocity air as the heating and cooling medium and low thermal inertia vessels ensures both temperature uniformity and rapid heat exchange with the sample, which benefits specificity of the reaction.

Both conduction and convection methodologies have limits and for example are inappropriate to permit PCR on a specimen under inspection using microscopy. In contrast, the present invention provides a new method for temperature control using the property of energy transfer from a controlled radiative source of electromagnetic energy which is amenable to microscopy applications. Electromagnetic radiations refer to a range of wavelengths or frequencies that are propagated by simultaneous periodic variations of electric and magnetic field intensity and that include gamma rays, X rays, ultraviolet, visible light, infra red, and radio waves to the longest radio waves. The present invention teaches the use of controlled preferably infrared energy extending from 750 nm to millimeter waves to produce molecular effects in biological specimens and/or biological systems. For example, one or more infrared laser beams provide a suitable source of controlled electromagnetic energy for the invention. Other light sources are possible alternatives, including one or more lamps, such as a filament lamp, an encased gas illuminator, and a pressurized gas lamp or electrical arc lamp that uses gas discharge to produce either a continuous or a discrete light spectrum that includes infra red waves.

Photothermal properties of laser light applied to promote temperature elevation of media and substrates are also known (Welch, A. J. et al., "Laser thermal ablation", *Photochemistry and Photobiology*, 53, 1991, 815–823). Laser thermal effects are used for ablation of various surfaces or tissues, with principal applications in medical sciences, such as dermatology treatments. Although technically attainable with either continuous wave or pulsed laser sources, laser ablation of tissues in medical applications is essentially reported for pulsed laser geometries which offer greater control over irradiation and permit minimized heat losses due to conduction. Water content of the target substrates plays a major role in the successful transfer of energy in the case of infrared laser sources. In the IR range of the electromagnetic spectrum, for wavelengths above 1300 nm, water, OH and amines are the dominant chromophores, and high contents in water clearly affects the local rate of heat generation at these wavelengths. Furthermore, the presence of water, or enhanced water content due to hydration, increases thermal conductivity and therefore heat conduction. Lasers that emit infrared light, for example at a wavelength of 10600 nm such as produced by a $CO^2$ laser, at a wavelength of 2940 nm from an Er:YAG laser, at 2100 nm from an Ho:YAG laser, at 1480 nm using a solid state diode laser, at a wavelength of either 1320 nm or 1064 nm from an Nd:YAG laser, and other lasers that emit within these boundaries of the spectrum have therefore been utilized for laser thermal applications. Technical requirements for medical laser-based instruments are principally established with reference to the penetration depth of the beam and its fluence. Since the penetration depth in the infrared range of the spectrum is determined by the relative absorption in water, laser wavelengths that coincide with an absorption peak of water constitute optimal choices.

Light energy and in particular laser energy in the field of microscopy is applied in a wide variety of applications. Laser beams are being used in combination with microscopes for the purpose of illuminating microscopic specimens or to produce specific effects. Typically, the beam is directed towards the back aperture of the objective lens which focuses the beam onto a localized area of the specimen. The same objective lens can be used to simultaneously observe the specimen. Precise positioning and alignment of the laser beam in multiple planes relative to the optical path of the microscope are made possible with adjustable lenses and mirrors. Laser sources are also coupled to microscopes via a flexible optical fiber that serves as a light guide.

Lasers coupled to microscopes are used as microscopy tools, e.g., for optical trapping and laser microablation. Manipulation of microscopic structures is discussed in U.S. Pat. Nos. 4,893,886; 5,170,890; and 5,283,417. In general, these patents discuss methods for trapping microscopic particles in a photon gradient, or for controllably damaging microscopic structures with laser energy. The ablative properties of laser microscope devices find applications in biology (Berns, M. W., et al., "Laser microsurgery in cell and development biology", *Science*, 213, 1981, 505–513; Rink, .et al, "1.48 μm Diode Laser Microdissection of the Zona Pellucida of Mouse Zygotes", *Proceedings SPIE*, 2134A, 412–422). U.S. Pat. No. 4,629,687 describes a method and apparatus for the positive selection of cells using a focused laser beam to kill unwanted cells. A technique called "Laser Capture Microdissection" includes picking out specific cells in vitro from a thin tissue section placed on a glass microscope slide by thermally modifying adhesive properties of a substrate (Emmert-Buck, M. R. et al., "Laser capture microdissection", *Science*, 274, 1996, 998–1001). Other applications describe the use of a microscope and laser assembly containing wavelength-selective mirrors for directing externally produced light into a microscopic sample for the purpose of stimulating fluorescence in the sample. With confocal microscopy, elaborate scanning illumination of a specimen is performed by a tightly focused spot of light (Matsumoto, B. and ramer, T., "Theory and applications of confocal microscopy", *Cell Vision*, 1, 1994, 190–198). Microscope and laser assembly devices are used to produce multiple photon excitation which involves the simultaneous absorption of two, three or eventually more laser photons by the same fluorophore. Multiple photon excitation techniques allow fluorescence emission to occur at a wavelength substantially shorter than the excitation and allow high resolution imaging without a confocal aperture.

A review of the literature demonstrates the usefulness of laser-microscopy technologies. A laser beam focused by the objective lens of a microscope can be used to illuminate or to transfer energy to a very small part of a microscopic target specimen. Although a variety of methods and devices have been described for both research and medical applications, the benefit of using a laser beam as a means to produce substantial energy delivery and thus temperature elevation, has not yet been investigated for applications with reference to the activation of thermo-enzyme reactions and in particular with reference to the amplification of nucleic acids with polymerase chain reaction. The prior art teaches and suggests the use of laser beams only for the destruction or ablation of cells, and at best provides means to limit damage to adjoining cells, which is essentially due to heat conduction. Thus, heretofore known devices disclose minimum heat deposition during short irradiation exposure times for ablation processes. However, it is an object of the present invention to be able to apply electromagnetic energy, such as a laser beam, to a thermo-enzyme reaction such as a polymerase chain reaction to purposely produce a sustained temperature elevation of a target specimen without ablation. In particular, we have unexpectedly found that the temperature elevation that can be anticipated from using a laser source in the infrared range of the spectrum is well within the boundaries applicable to produce certain temperature-sensitive transformation of biological systems such as with activation of enzymes or heat shock proteins or with PCR reactions.

SUMMARY OF THE INVENTION

The inventive method of activating a thermo-enzyme reaction, such as a cycling reaction, includes the step of applying electromagnetic energy to a target to produce a rapid elevation in the temperature of at least a portion of the target, which does not cause destruction or ablation of cells, chromosomes and other targets as brought about by heretofore known laser application methods. The apparatus for accomplishing this comprises a vessel that is adapted to contain a target, means for applying electromagnetic energy to the target, and means for controlling the electromagnetic energy in such a way as to produce a rapid elevation in the temperature of at least a portion of the target. In the context of the instant application, the target refers to a specimen, or a solution or reagent containing reactive material. In particular, the target refers to the chemically reactive region or zone that is spatially delimited by the three-dimensional path occupied by the beam of applied electromagnetic energy.

The present invention is applicable in general to a number of thermo sensitive molecular functions. For example, the present invention is applicable to treating experimental systems, cells, chromosomes, or to treating at least a portion of a microscopic target with temperature variations for the purpose of producing temperature-sensitive effects and traces formations such as with the synthesis of nucleic acid polymers or with the production of heat shock structural proteins and/or with the activation of enzymatic functions. In systems and methods according to certain aspects of the present invention, in treating specimens and media for the purpose of amplifying specific polymers of nucleic acids into identical polynucleotides using polymerase chain reaction (to replicate the specific polymers of nucleic acids or other polymers) or for the purpose of activating other thermo-enzyme reactions with electromagnetic energy by directing a preferably infrared laser beam to the target area, rapid elevation and stabilization of temperature is achieved as a result of absorption of laser energy by water molecules. In certain aspects, such a beam is attained by using either a continuous wave or a pulsed laser source, with a pulsed laser permitting a pulse duration of as short as $10_{-9}$, $10^{-12}$, and even $10^{-15}$ seconds. The laser source utilized may comprise a plurality of laser sources and is either single mode or multiple modes, with emission either centered on a single wavelength of light or with a plurality of wavelengths of light. The energy distribution of the incident laser beam can be of a Gaussian type profile. The power of the laser or lasers can be controlled by shaping the beam of the laser that is to impinge upon the material that is to be affected by the laser, by changing the power output of the laser, and/or by altering the pulse width of the laser while retaining constant laser intensity. In certain aspects of the present invention the laser source utilized is preferably in the infrared range of the electromagnetic spectrum, possibly from 750 nm to millimeter wavelengths. In certain aspects of the present invention, the wavelength of the infrared laser beam coincides with one or more absorption peaks for water, thus maximizing heat transfer. The systems and methods described in the present invention accomplish laser-generated incremental temperature elevations of an aqueous solution, up to temperatures suited to promote denaturation of template DNA, reliable primer annealing and optimum extension and polymerase activity during the recurrent phases of polymerase chain reaction, which is a function of the laser beam intensity, wavelength, profile and distributed photon density, which can be controlled and/or improved optically, electronically and/or spatially to favor one, several or all phases of the polymerase chain reaction. Possibly, laser energies delivered are effective to promote vaporization of water.

The present invention also teaches a method for applying efficient (focused) laser energy to a microscopic specimen under inspection, or to an area of a target substrate or solution of microscopic dimensions, for the purpose of activating a thermo-enzyme reaction such as amplifying nucleic acids into polynucleotides using polymerase chain reaction. The method, in one aspect, includes applying laser energy to a microscopic target under inspection and directing or focusing the output beam to the specimen through a microscope objective lens. In one aspect, such systems and methods according to the present invention are used to produce activation of a thermo-enzyme reaction such as to produce amplification of nucleic acids into polynucleotides using the polymerase chain reaction in selected locations of microscopic specimens of biological origin such as with cells, chromosomes, and tissues sections or biopsies which are used for research or diagnostic purposes.

BRIEF DESCRIPTION OF THE DRAWINGS

The invention and its practice will be further described with reference to the accompanying drawings, in which.

DESCRIPTION OF PREFERRED EMBODIMENTS

In presently preferred embodiments of the invention, the source of electromagnetic energy may be at least one laser or at least one lamp producing suitable infrared radiations. Preferred embodiments of the invention that make use of lamps such as a filament lamp, an encased gas illuminator, and a pressurized gas lamp or electrical arc lamp that uses gas discharge to produce either a continuous or a discrete light spectrum that includes infrared waves, are compatible in practice with the general structure of known lamps. It will be obvious to one skilled in the arts that although the following discussion emphasizes exemplary embodiments that make use of infrared laser sources, it is applicable to embodiments of the invention with lamp structures.

Figure 1:
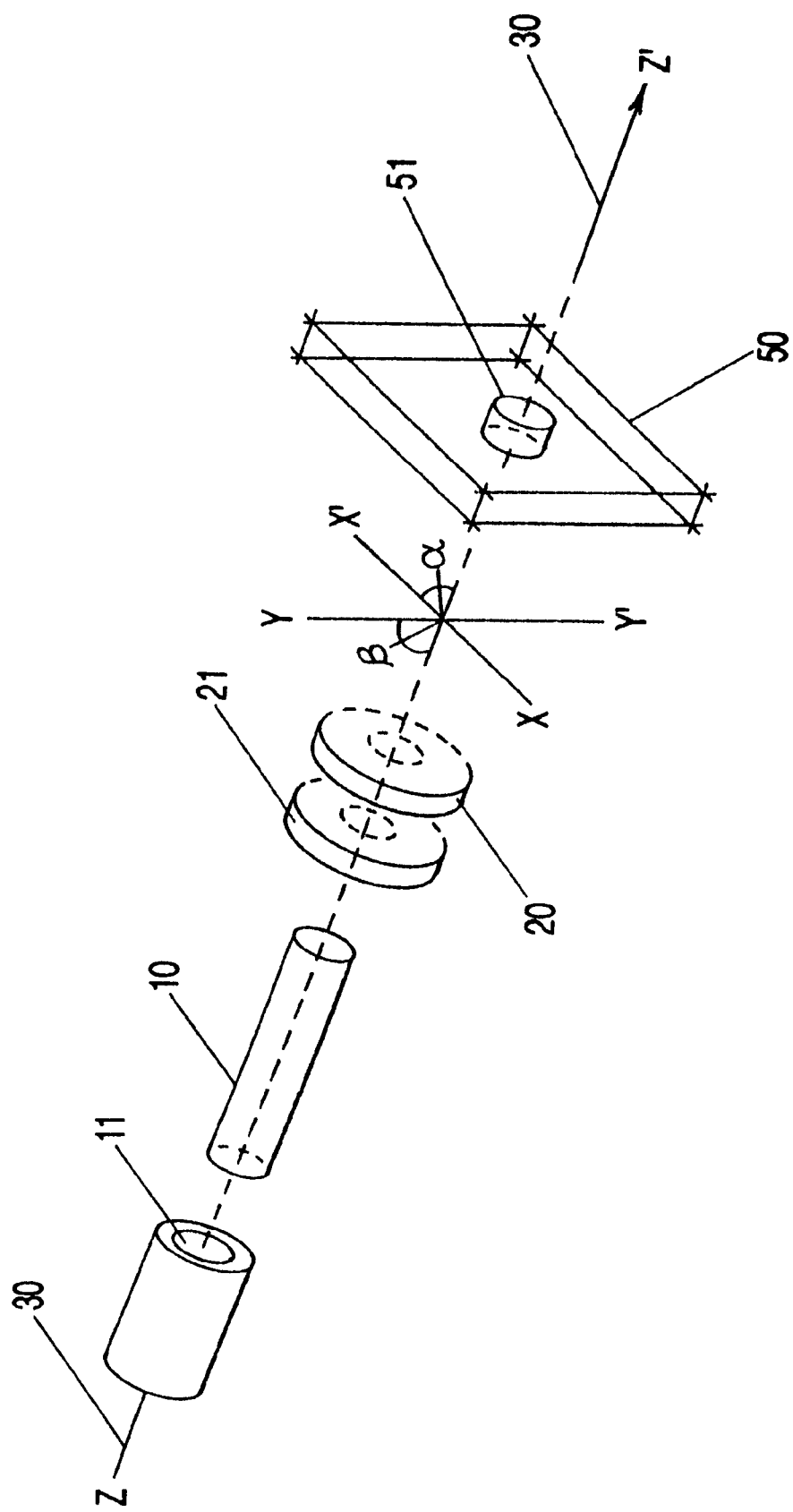
FIG. 1 is a schematic representation of an exemplary system useful with methods according to the present invention, and shows a source of electromagnetic energy such as a laser, a beam conditioning optic, an incident laser beam, and the target to be irradiated for the purpose of activating a thermo-enzyme reaction or producing nucleic acid amplification with polymerase chain reaction.

Referring to FIG. 1, a system according to the present invention has a laser beam 10 emitted by a laser source 11 and possibly directed towards optical control devices 20 and 21 for controlling both spatial distribution and position of the output laser beam 10 with reference to a target 51. By preference, the output laser beam is collimated afterward by optical control devices 20 and 21. Preferably, the distribution of the laser source 11, the laser beam 10 and optical control devices 20 and 21 are parallel and aligned to an axis 30 and the propagation of the output laser beam is oriented along the Z–Z' direction. The axis 30 of the laser beam 10 is substantially normal to the plane defined by the axes X–X' and Y–Y'. The laser beam is applied to irradiate a target area 51 within a vessel 50 containing the reagents for polymerase chain reaction. In varying embodiments for the invention, the target 51 is either an aqueous solution or a biological specimen or both. Laser irradiation of the target 51 results in temperature elevation due to the absorption of laser energy.

Alternatively, the direction Z–Z' of the output laser propagation is not orthogonal to the plane defined by the axes X–X' and Y–Y', but with varying angles $\alpha$ and $\beta$. The laser source 11, the vessel 50 and target area 51 may be placed on differing axes. In varying embodiments for the invention, one or more mirrors (not shown) are placed on the path of the laser beam 10 to direct the beam efficiently and in a proper direction toward the vessel 50 and target area 51.

The system of FIG. 1 and similar embodiments (e.g., but not limited to, the addition of a mirror) is compatible in practice with the general structure of known lasers and laser optical devices. Any suitable laser may be used according to the present invention, including, but not limited to, solid-state lasers, gas lasers, dye lasers, semi-conductor lasers, diode lasers, and diode or lamp pumped solid-state lasers. The present invention envisions several ways to meet particular technical requirements. To account for the potential asymmetric divergence angles from the output beam, such components as beam conditioning optics of various dimension, size or shape, spatial filtering device or optical fiber(s) coupled to the laser source may be used according to the present invention. The irradiance distribution of the beam is, in certain aspects, symmetrical, generally circular but possibly ovoid, toroidal or even multiangular in a cross section through the beam which can be realized by a laser operating either in a single or multiple mode (e.g. laser operation $TEM_{00}$ or with combined $TEM_{00}$ and $TEM_{01}$). In a preferred embodiment for the present invention, the wavelength of the output laser beam is in the infrared range of the electromagnetic spectrum, from 750 nm to millimeter wavelengths. In a preferred embodiment for the present invention, the wavelength of the output laser beam coincides with a peak of absorption for water.

Figure 2:
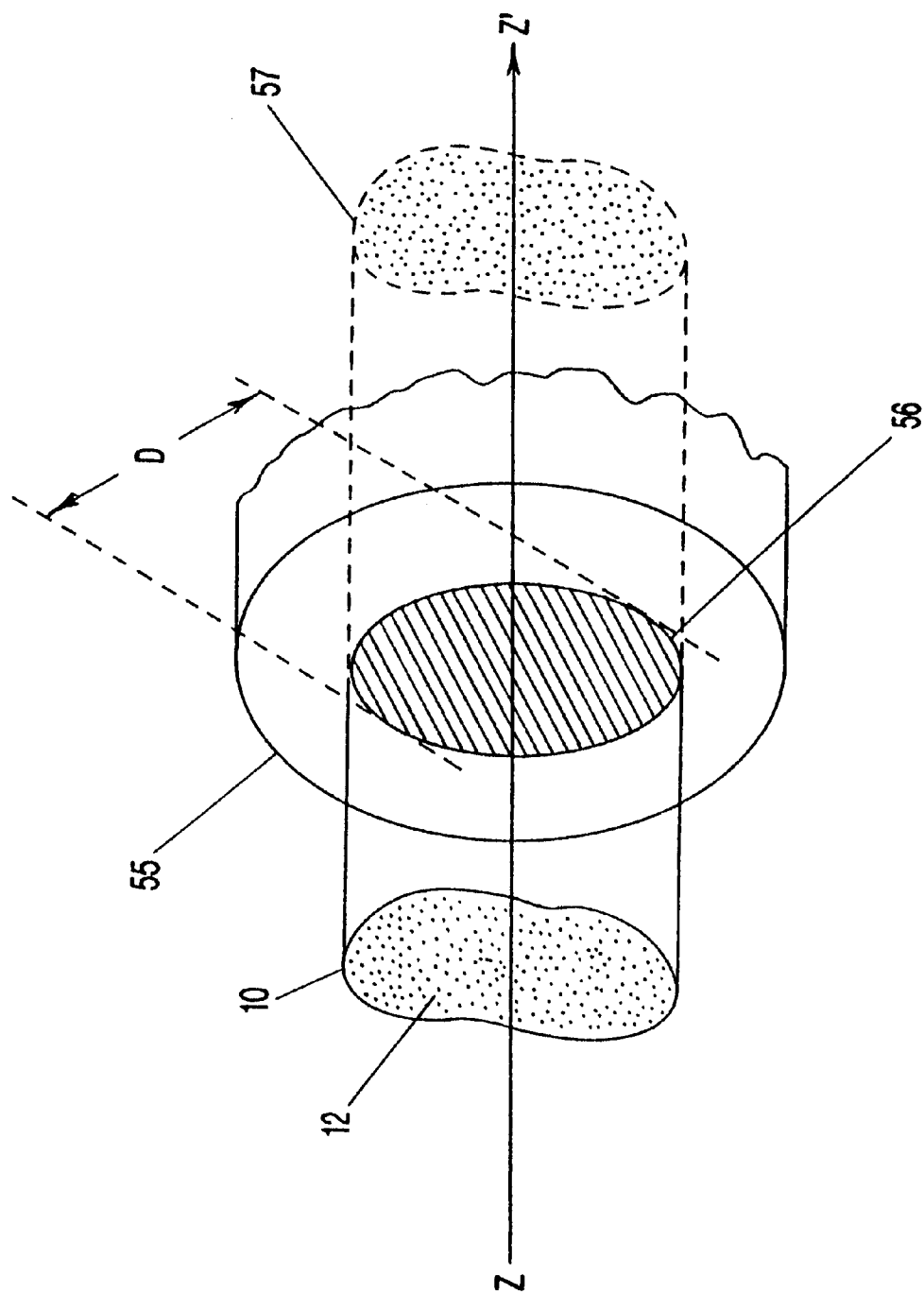
FIG. 2 is a side perspective view illustrating the irradiance of an example incident laser beam with reference to a vessel containing an aqueous solution and reagents such as for polymerase chain reaction.

Referring to FIG. 2, the laser beam 10 is utilized to produce localized elevation of temperature of a localized area within a vessel 55. In FIG. 2, a typical circular or nearly circular irradiance distribution 12 with diameter D is depicted for an output laser beam 10 with Z–Z' direction of propagation. The output laser beam 10 intersects the window of the vessel 55 on which a diametric slice 56 circumscribes the beam profile. In FIG. 2, the vessel 55 is not shown in its entirety; other embodiments of the invention may use vessels of either greater or smaller dimensions and with varying shape and size. The output laser beam 10 penetrates the vessel 55, and the contents (not shown) of the vessel 55 are exposed to the distribution of laser energy 57. The energy delivered is absorbed by the contents of the vessel, preferably rich in water molecules, over a substantial proportion of the beam. In other words, the fraction of the beam with laser energy that is allowed within the vessel is converted to heat by absorption phenomena. It will be evident to one skilled in the art who now has the benefit of the teachings, realizations, disclosures, and suggestions of the present invention that the spatial distribution of laser energy to the contents within the vessel can be easily adjusted using devices such as, but not limited to, various optical devices, spatial filtering devices, focusing lenses, converging and diverging lenses, mirrors, solid optical fiber waveguides, and hollow waveguides, and that the periphery of the beam can be adjusted to match the width and shape of a specific vessel or target substrate. Emission of an incident laser beam can be at the distal end of one of the aforementioned waveguides. Other light guide devices, such as micropipettes, can also be used to focus the radiation to a very small volume.

Other embodiments of the invention may use several laser sources and laser beams to simultaneously deliver laser energy within the same vessel. It will be evident to one skilled in the art that multiple laser sources or laser beams may vary with reference to the laser energy distributed, beam profile, mode of operation and wavelength.

Although preferred embodiments of the present invention may be applicable to produce temperature variations suitable for a number of thermo-sensitive reactions within biological systems, the discussion herein emphasizes the activation of a cyclic reaction to produce nucleic acid polymers since indications for such fundamental examples are relevant to other uses of the invention. In a preferred embodiment of the present invention, laser energy applied to the content of a vessel and translated into heat energy is used for polymerase chain reaction. In one aspect, laser energy is translated into heat for the denaturation phase of the template DNA molecules. In one other aspect, laser energy translated into heat is applied for primer annealing. In one other aspect, laser energy is translated into heat as required for the elongation phase of the PCR reaction. According to the present invention, delivery of infrared laser energy which is absorbed by water molecules permits the rapid elevation of temperature within the target area of laser irradiation. Rapid temperature changes are very important to produce highly reliable and clean or uncontaminated PCR products. Reducing the time necessary to reach optimum temperature levels for each phase of the PCR reaction is key to reducing the amount of nonspecific products because less time is then available for primer extension at non-specific annealing sites. The use of laser energy to promote temperature elevation within the reaction vessel is unsurpassed with reference to rapidity since temperature transitions occur at the molecular level, by direct absorption of laser energy, without the need to control temperature shifts of massive heater elements or of voluminous fluidic buffers as required in heretofore known processes requiring bulk conduction and convection mechanisms. Pursuant to the present invention, temperature elevation and complementary phases of the polymerase chain reaction are spatially limited by the irradiance energy distribution of the incident laser beam and, possibly, by the lateral thermal conduction properties of the target system or surrounding aqueous buffer. Means to control the electromagnetic energy include analog and digital electronic devices, shutters, filters, or combinations of such devices that make it possible to produce rapid elevations and lowering of temperature of at least a portion of a target. The diffusivity of heat in a small volume is crucial for the kinds of reactions that are contemplated by the present invention. If one imagines a group of spheres of increasing size, as the sphere volume increases so does the surface area of the sphere. The ratio of the surface area to volume is important in the heating up and the dissipation of that heat by passive conduction from the sphere to its surrounding environment. As the size of the sphere increases, the surface area to volume ratio increases by the relationship (⅓r). For a sphere with a radius r=one micron, the ration is 1:3; for a sphere with radius r =10 microns, the ratio is 1:30. The consequence of the physical laws governing the heating and dissipation of heat by diffusion is that large volumes take longer to heat, and also take longer to cool. By limiting the target or region of reactivity to a very small volume, the rate at which the reaction can be repeated will be much faster than if the target region were comparatively larger.

Pursuant to one exemplary embodiment, the present invention teaches a method to elevate temperature within the PCR reaction vessel to levels respectively suited for denaturation, annealing and extension phases, using a preferably infrared laser source. Since the reaction vessel in which are placed the PCR reagents and specimen of biological origin, such as isolated cells, chromosomes, DNA, RNA or a fragment thereof, a tissue section, or a biopsy, contains essentially water, it is appropriate to refer to the temperature elevation mechanism in the vessel upon laser irradiation as a thermal event driven by the absorption properties of water in the infrared wavelengths. Preferred embodiments of the invention make use of a laser source at a wavelength that coincides with an absorption peak for water for optimum energy transfer. If the contents of the PCR reaction vessel are at the initial temperature Ti, sufficient laser energy is necessary to bring the water component to a specific temperature with reference to denaturation Ts-d, annealing Ts-e and extension Ts-e phases. Since PCR reactions require temperature control over a wide range of temperature, in one aspect, a regulated laser source according to the present invention provides sufficient heat to cover that full range of temperature. In one aspect, the laser source provides sufficient heat to bring the water to the critical temperature Tc (100° C. for water). As an example, it is known that for water at 37° C., $0.25 J/mm^3$ of laser energy are necessary to heat water to 100° C. A generalization of the threshold fluence $[J/mm^2]$ and of the energy [J] that must be supplied by the laser radiation to reach the specific temperature requirements Ts-d, Ts-a and Ts-e $[J/mm^3]$ is formulated by assuming that the output laser source has a uniform irradiance profile $[W/mm^2]$ and pulse duration [s] (in the case of a pulsed laser source), over a known area $[mm^2]$ and that the laser energy is uniformly distributed along the penetration depth [mm] within the reaction vessel. It will be clear to one skilled in the art that a significant amount of the heat generated by the absorption of the laser light in water is conducted axially and radially away from the laser beam within the reaction vessel. Diffusion of heat to the surrounding area of direct target irradiation may occur resulting in sub-optimum temperatures in these locations and can be minimized with specific output laser beam distribution tactics or using specific reaction vessels. Distribution tactics for delivering laser energy within the reaction vessel may include devices for controlling relative displacement of the output beam with reference to the vessel and may be accomplished with action on mirror assemblies and associated lenses for producing a laser beam steering or scanning mechanism. Continuous pattern or incremental steps of displacements for the laser beam direction of propagation with reference to the vessel may be thus produced. Specific reaction vessels, in certain aspects, are preferred with surface area of dimension compatible with the width of the laser beam in such a way that the periphery of the beam is adjusted to match the width of the vessel. Such vessels can be, but are not limited to, dishes, slides, tubes, and other containers made of material, such as plastic or glass, that is transparent to the wavelengths of the electromagnetic energy that is utilized.

Figure 3:
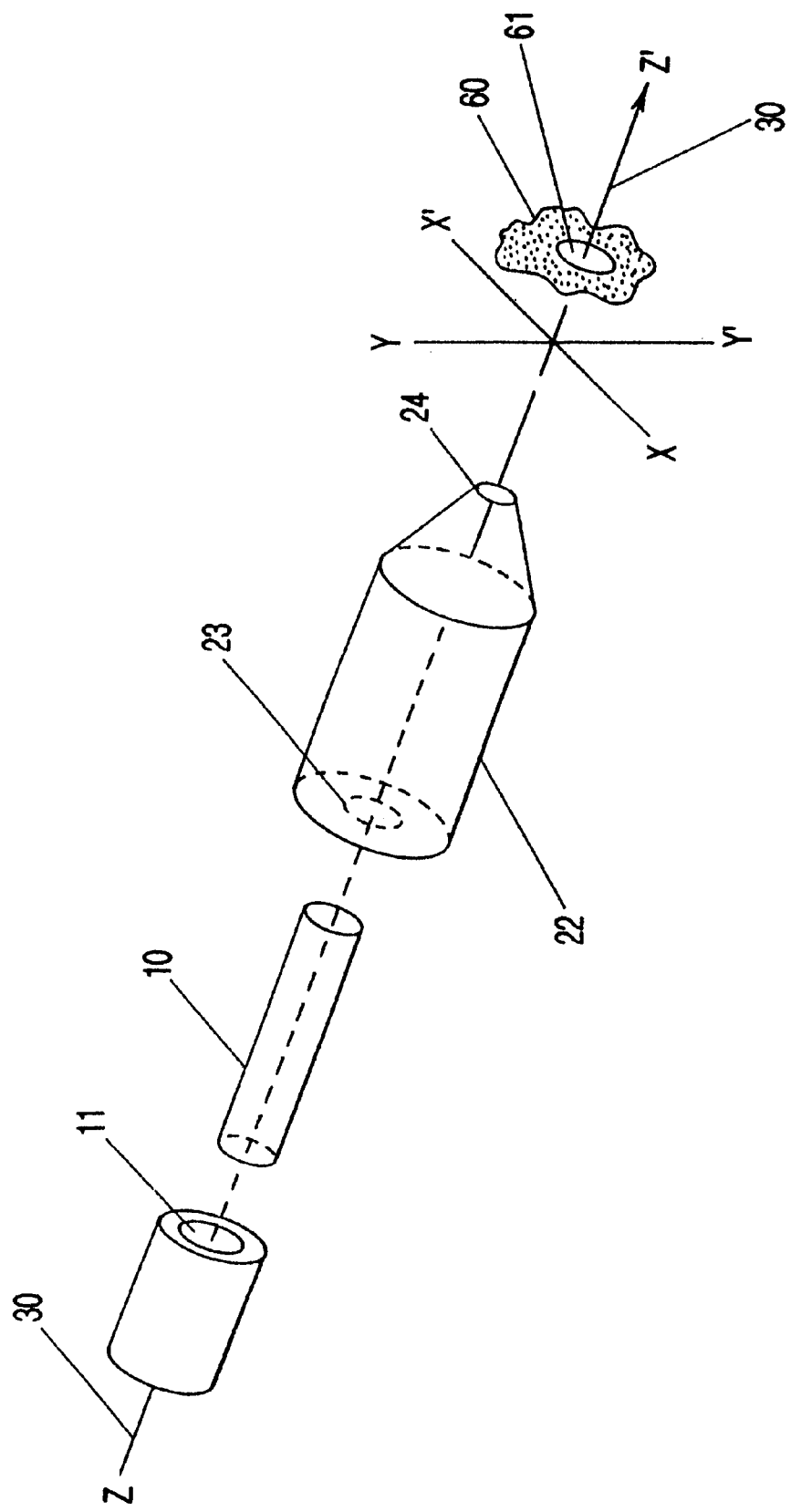
FIG. 3 is a schematic representation of an exemplary system useful with methods according to the present invention, and shows a laser source (as a source of electromagnetic energy), a beam conditioning optic, an incident laser beam, an objective lens and the target to be treated for the purpose of activating a thermo enzyme reaction or producing nucleic acid amplification with polymerase chain reaction with reference to microscopy applications.

In the system shown in FIG. 3, according to the present invention with reference to microscopy applications, a laser beam 10 emitted by a laser source 11 and directed towards the back aperture 23 of an objective lens 22 is focused on a target substrate 60. By preference, the output laser beam 10 is collimated before reaching the back aperture 23 of the objective lens 22. In certain aspects of the invention, a typical irradiance distribution diameter of the laser beam 10 is identical or nearly identical to the diameter of the back aperture 23 of the objective lens 22. It is clear that the periphery of the beam, where the total energy delivered eventually drops, can easily be truncated using the back aperture of the objective lens itself to mask off the expendable portion of the beam. As indicated in FIG. 3, the periphery of the beam is adjusted to match the width of the back aperture of the lens which is representative of its functional optical path. The beam axis 30 is along its direction of propagation Z–Z' and is centered to the center of the optical path of the lens. In this particular aspect, a full fill of the optical path of the lens by the incident laser beam is arranged which provides centered laser beam output from the front aperture 24. Other embodiments of the invention may use laser beam diameters of either greater or smaller diameter of the lens' back aperture. The option and advantages to using a laser beam of varying diameter is well known to those skilled in the art; a greater laser diameter is advantageous when spatial filtering is required, a smaller laser beam diameter is preferred to facilitate movement of the beam, such as for scanning the target substrate. Preferably, the distribution of the laser source 11, the laser beam 10 and the objective lens 22 are parallel and aligned to an axis 30 and the propagation of the output laser beam is oriented along the Z–Z' direction. The axis 30 of the laser beam 10 is substantially normal to the plane defined by the axes X–X' and Y–Y'. The laser beam is applied to irradiate a limited area 61 of a target substrate 60. In varying embodiments for the invention, the target 60 is a solution containing the reagents for PCR, or a specimen from biological origin such as, but not limited to, a cell, a chromosome, a fragment of DNA or RNA, a tissue section or a biopsy immersed in a solution containing the reagents for PCR. Laser irradiation of the target substrate 60 results in temperature elevation due to the absorption of laser energy over the area of direct illumination 61 and along a penetration depth (not shown) within the reaction vessel (not shown).

Alternatively to the system of FIG. 3, the direction Z–Z' of the output laser propagation is not orthogonal to the plane defined by the axes X–X' and Y–Y'. The laser source 11, the target substrate 60 and surface area 61 for laser irradiation may be placed on differing axes and one or more mirrors (not shown) may be placed on the path of the laser beam 10 to direct it efficiently and in a proper direction toward the target substrate 60.

The system of FIG. 3 and similar embodiments (e.g., but not limited to, the addition of a mirror) are compatible in practice with the general structure of known laser devices associated to microscopes. Pursuant to one exemplary embodiment of the inventive apparatus or system, a microscope device is provided that has at least one objective lens and a specimen holder or vessel to contain both the specimen and the components of the thermo-sensitive enzyme such as the components of the polymerase chain reaction on the microscope device. A specimen viewing device is also provided on the microscope, wherein the objective lens could be used simultaneously to focus the incident laser beam and to view the microscopic specimen that is under inspection. Also provided are a control device for controlling the position of the output laser beam with reference to a target specimen or substrate, as well as a device to control the position of the vessel on the microscope device relative to the laser beam. In particular, the at least one objective lens can be of suitable magnification factor and optical characteristics to allow simultaneous irradiation of a specimen for the purpose of promoting activation of a thermo-enzyme reaction such as polymerase chain reaction and for viewing the specimen under inspection. Alternatively, a separate specimen viewing device can be provided for viewing the selected microscopic specimen, and can, for example, be a magnifying glass, eyepieces, or video imaging system. With such a system, a lens of the microscope device will focus a laser beam through the observation window of the reaction vessel, onto a target that will be from a fraction of a micrometer to a few hundred microns in diameter. Assuming a spherical target of 100 micrometer diameter or $1.25 \times 10^{-7}$ ml volume, dissipation of heat over a temperature gradient from 100 to 25° C. ambient temperature should theoretically take less than 1 second.

Figure 4:
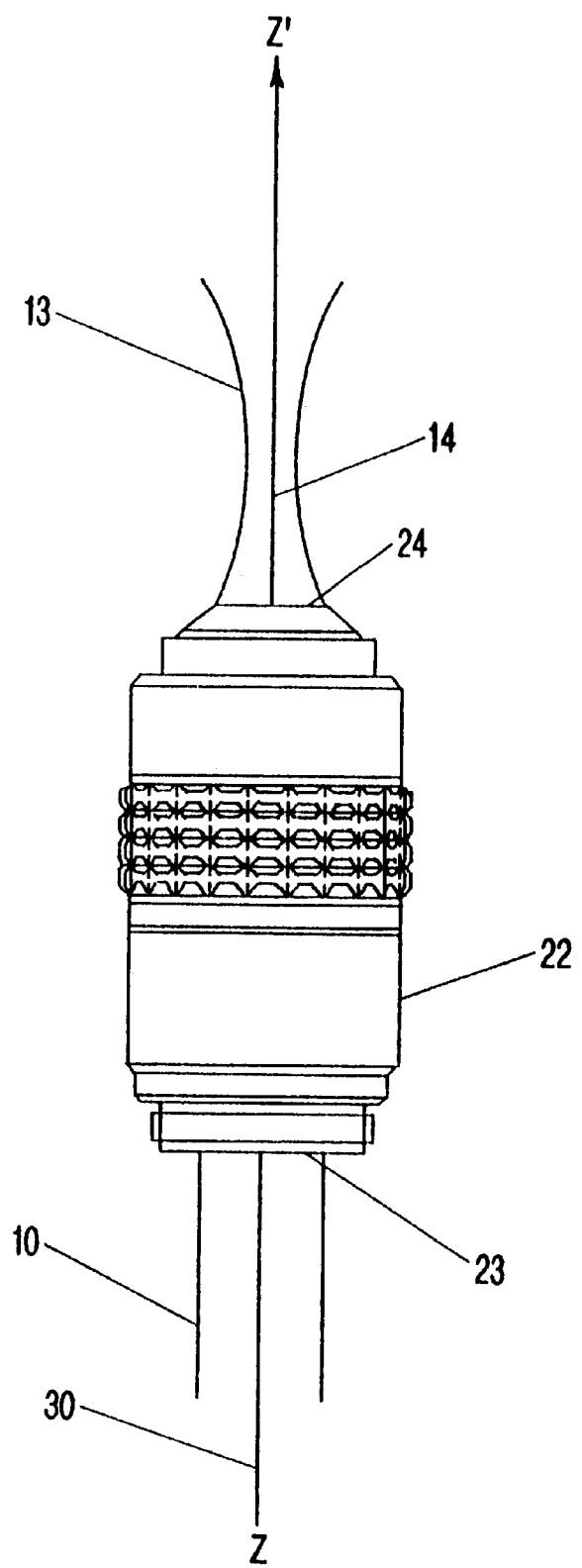
FIG. 4 is a side view illustrating the irradiance of an example incident laser beam focused using an objective lens.

FIG. 4 shows a side view of the beam irradiance distribution for a laser beam focused by an objective lens according to the system described with reference to FIG. 3. The example of FIG. 4 depicts a symmetrical and collimated laser profile directed perpendicularly towards the back aperture 23 of the objective lens 22. The optical path of the lens is filled up by the incident laser beam for optimizing illumination efficiency, in other words the fraction of the beam allowed through the lens. The focused laser energy distribution profile 13 delivered at the front aperture 24 for the lens is shown uniform and symmetrical over the substantial proportion of the width of the beam. Although not depicted in FIG. 4, it is assumed that, in certain aspects, the energy distribution drops at the periphery of the beam such as when using a laser source with typical Gaussian distribution representative of laser output distribution. The example of FIG. 4 depicts a symmetrical laser profile relative to its diametric axis, location of which is indicated by the axis 30. The peak of focused laser energy is centered on the focus point 14 for the laser beam and the gradient of energy progressively decreases as the beam profile departs towards the beam radius. The power available in the Gaussian type of laser distribution provides increasing energy towards the center of the beam.

It will be apparent to one skilled in the art and who benefits from the teaching of the present invention that delivery of electromagnetic or laser energy to a generic microscopic specimen or to a microscopic area of a solution containing reagents for PCR reaction, is accomplished by focusing effects from the objective lens. The volume of efficient thermal treatment is limited by the area of laser illumination with possible diffusion effects and by the penetration depth within the vessel or specimen. The total amount of energy delivered is accumulated by controlling irradiation duration and wavelength and is a function of the optical properties of the specimen in addition to laser power. The laser beam power is a factor that may be controlled with the use of regulated power, and/or by using appropriate optical filtering devices. Cooling during each cycle is mediated by the high thermal diffusivity of water and the small volume being affected by the laser when it is on. Because both the thermal capacity and thermal diffusivity of water are high (relative to air), the combined effect of highly focused, transient, laser illumination to effectively elevate the temperature of a substrate during precise periods of time, and the high diffusivity of water, provides an effective way of rapidly lowering the temperature in a highly localized fashion so that for polymerase chain applications denaturation, annealing, extension, and polymerization of DNA can be optimized. The lowering of the temperature by thermal transfer by water from the localized area heated by the source of focused electromagnetic energy such as a laser, and the precise control of the duration of laser activation of the process, provide the means to efficiently achieve fast and high specificity products during the polymerase chain reaction by laser.

In one aspect of the invention, the microscopic specimen is maintained at an initial background temperature using a heater element attached to the microscope instrument and the effect of the laser beam is limited for rapid and sharp temperature elevation as required for specific thermoenzyme activation such as specific phases of the PCR reaction.

To one of ordinary skill in this art who has the benefit of this invention's realizations, teachings, disclosures and suggestions, other purposes and advantages will be appreciated from the non-limiting examples of use given here for the purpose of illustration. Use of laser energy with PCR reaction or other thermal enzymatic reactions for various microscopic specimens will benefit from the invention. Polymerase chain reaction with laser energy may be used for analysis and diagnosis or for preparative applications of genetic material. In addition, other thermally-induced reactions, such as various discovered enzymes and/or heat-shock proteins, may be treated in a like manner and the embodiments may be used for diagnostic purposes, for genetic mutations, for gene therapy, for diagnosis of pathogens, for detection of diseases such as cancer, HIV or other viral infections, or for detection of specific cell or chromosome recognition sites. Additionally, other thermally-induced changes in genetics may be achieved and adjacent technologies used to detect the changes.

What we claim is:

1. A method of thermally inducing a reaction, including the step of applying electromagnetic energy in the infrared range to a target in the form of an aqueous solution or a biological specimen or both to produce a rapid elevation in the temperature of at least a portion of said target.

2. A method according to claim 1, wherein said elevation of temperature of at least a portion of the said target is defined by the spatial distribution of photons of said electromagnetic energy.

3. A method according to claim 1, wherein said step of applying energy comprises raising the temperature of said target to a level sufficient for specific synthesis or activation of certain bio-molecules including structural heat shock proteins and/or enzymes.

4. A method according to claim 1, wherein said step of applying energy comprises raising the temperature of said target to a level sufficient for activating a polymerase chain reaction for the purpose of producing copies of nucleic acid polymers.

5. A method according to claim 1, wherein said electromagnetic energy is laser energy provided via a laser beam supplied from at least one laser source.

6. A method according to claim 1, wherein said electromagnetic energy has a wavelength in the infrared range from 750 nm to millimeters.

7. A method according to claim 6, wherein said infrared radiation coincides with at least one absorption peak for water.

8. A method according to claim 5, wherein said laser beam is used in a pulse mode or in a continuous wave mode.

9. A method according to claim 1, wherein said electromagnetic energy is light energy provided via at least one of the group consisting of filament lamps, encased gas illuminators, and pressurized gas and electrical and lamps that use gas discharge to produce either a continuous or a discrete light spectrum that includes infrared waves.

10. A method according to claim 1, wherein said step of applying electromagnetic energy comprises applying said energy in such a way that a discrete elevation in temperature is achieved, and after a given period of time, a further discrete elevation in temperature is achieved, wherein further elevations in temperature are achieved as necessary.

11. A method according to claim 1, which includes the step of controlling spatial distribution of said electromagnetic energy relative to said target.

12. A method according to claim 5, which includes the step of controlling the position of said laser beam relative to said target.

* * * * *